(12) United States Patent
Hollis

(10) Patent No.: US 6,895,266 B1
(45) Date of Patent: *May 17, 2005

(54) LASER LIGHT EMITTER SURGICAL SITE LOCATING DEVICE AND METHOD

(75) Inventor: J. Marcus Hollis, Milton, FL (US)

(73) Assignee: Vector Medical Inc., Milton, FL (US)

( * ) Notice: Subject to any disclaimer, the term of this patent is extended or adjusted under 35 U.S.C. 154(b) by 449 days.

This patent is subject to a terminal disclaimer.

(21) Appl. No.: 09/816,778

(22) Filed: Mar. 26, 2001

(51) Int. Cl.$^7$ ................................. A61B 5/05
(52) U.S. Cl. ................... 600/407; 600/424; 600/473; 606/96
(58) Field of Search ................... 600/407, 473, 600/424, 476, 310, 160, 178, 182; 606/96

(56) References Cited

U.S. PATENT DOCUMENTS

| | | | |
|---|---|---|---|
| 4,444,185 A | 4/1984 | Shugar | 128/305.3 |
| 4,621,628 A | 11/1986 | Brudermann | 128/92 VD |
| 4,898,175 A | 2/1990 | Noguchi | 128/634 |
| 5,423,321 A | 6/1995 | Fontenot | 128/664 |
| 5,540,691 A | 7/1996 | Elstrom et al. | 606/64 |
| 5,879,306 A | 3/1999 | Fontenot et al. | 600/473 |
| 5,902,247 A | 5/1999 | Coe et al. | 600/476 |
| 5,906,579 A | 5/1999 | Salm et al. | 600/424 |
| 6,081,741 A | * 6/2000 | Hollis | 600/424 |
| 6,516,216 B1 | * 2/2003 | Fontenot et al. | 600/473 |

* cited by examiner

Primary Examiner—Henry Bennett
Assistant Examiner—Camtu Nguyen
(74) Attorney, Agent, or Firm—Jim Zegeer

(57) ABSTRACT

An apparatus and method for guiding a surgical instrument within and around the human body. The invention employs a light emitter and an array of light sensors and a display to accurately locate an anatomical feature into which the light emitter has been placed. Laser or LED light emitted from an emitter, conveyed by a light conduit, is detected after passing through a thickness of bone and/or soft tissue by the sensor array. The signal from the sensor array is processed-and information indicating the relative direction of the emitter from the sensor is displayed. The light can be directed by a mirror or by bending the end of the light conduit.

7 Claims, 4 Drawing Sheets

LASER LIGHT EMITTER SURGICAL SITE LOCATING DEVICE AND METHOD

FIELD OF THE INVENTION

This invention related to my U.S. Pat. No. 6,081,741 issued Jun. 27, 2000 entitled INFRARED SURGICAL SITE LOCATING DEVICE AND METHOD and incorporated herein by reference.

The present invention relates to the field of surgery, in particular to the more precise guidance of surgical tools and locating anatomical features with a laser light emitter, light guide, mirrors, an array of sensors and a direction display.

BACKGROUND OF THE INVENTION

During surgery it is necessary to locate a particular anatomic structure. This is often done by creating an incision through the skin and directly observing the structure. In some situations it is possible to advance a small tube or catheter into the structure of interest from a remote location such as through a vessel, cavity, or duct.

Light-emitting catheters have been used to produce an area of illumination on the surface of the body in order to locate a specific anatomical area. For example, U.S. Pat. No. 4,444,185 permits a tracheotomy by providing a device placed into a tracheal tube which emits outwardly directly light through the trachea and surrounding soft tissue as a means of locating the trachea. Also, in U.S. Pat. No. 5,540,691, a method and device are described for locating a hole in an intramedullary rod inserted into a long bone by observing illumination on the surface of the body provided by a light emitter placed within the intramedullary rod. U.S. Pat. No. 4,898,175 provides a method of observing images produced by light passed through body tissue to the surface. U.S. Pat. No. 5,423,321 presents a device a method for avoiding internal organs by placing a catheter which emits light along its length within the organ and placing a light sensor on the surgical tool and a means to indicate when light from the emitter is detected indicating proximity to the organ to be avoided.

However, none of the references cited above employ an array of sensors to precisely and accurately determine the direction of the emitter with respect to the sensor or to confirm precise and accurate centering over the emitter at low cost.

U.S. Pat. No. 5,423,321, "Detection of Anatomical Passages Using Infrared Emitting Catheter," is a method for determining proximity to anatomical structure by placing a single emitter or line or line of emitters in structure and determining proximity to surgical instrument by measuring intensity of light emitted. U.S. Pat. No. 5,423,321 merely teaches the use of a single light sensor to serve as an indicating of the proximity of the emitter. It does not provide or suggest precise and accurate information on the direction of the emitter from the surgical tool. It does not have an array of sensors or emitters. It does not give direction of source from the emitter.

U.S. Pat. No. 5,540,691, "Optical Distal Targeting Method for an Intramedullary Nail," is an apparatus for detecting the location of transverse holes of an intramedullary nail and aligning a drill with the holes. This system consists of a light source which is passed down the center of the intramedullary rod and a video system which is sensitive to infrared light which captures an image of the light transmitted through the transverse hole in the rod. The light simply shines out toward the surgeon who attempts to line up the drill by centering it on an area of light coming out of the hole. The infrared is visualized using either a video system sensitive to IR light or goggles which are sensitive to infrared. U.S. Pat. No. 5,540,691 requires the surgeon to wear night vision goggles or employ a video device which displays an image on a screen which shows the light transmitted through the tissue. There is no mechanism for automatically finding when the drill is accurately centered or oriented. The surgeon would need to divert his eyes to the video screen to judge when the light intensity was centered around the drill. Therefore, this system is much more difficult to use than the device of this invention. It would be much more difficult to accurately determine the center of a hole using the video system. The system and method of the invention is also much simpler and cheaper since one would not have to use a video system.

THE PRESENT INVENTION

The present invention provides precise and accurate information of the direction of emitter from sensor and indicates the precise center of the emitter and the direction of relative movement between the sensor array and emitter for precise and accurate positioning and orientation or alignment purposes. Thus, the invention can find an anatomical position and orientation for a surgical procedure much faster and easier.

By using an array of inexpensive sensor elements, the center of the emitter can be quickly and precisely located with a minimum of trial and error, and then for alignment purposes, it provides the relative direction and relative amount of movement to rapidly achieve accurate alignment or orientation.

The surgical locating device previously disclosed in my U.S. Pat. No. 6,081,741 utilizes a light emitter in a catheter form and a detector. The light source could be one of many types including LED, laser, gas vapor bulb or incandescent bulb. The present invention provides an emitter with a laser light source. The laser emitter will allow for a narrower light beam than the LED light source. This will result in decreased spread of the light. This will produce a more focused spot of light and an increased gradient of light at the sensor array, thereby enabling a more precise locating of the emitter with the detector.

The present invention also provides a light conduit. The advantage of using a light conduit to transmit the light is that it will enable the tube to be a smaller diameter for a given light intensity and will enable a variety of light sources of high intensity to be used with little regard to the size of the source.

The laser light source and the light conduit can be used together or independently.

The preferred embodiments of the emitter are as follows: An elongated tubular member is provided which can be made of a transparent material. At one end of the tubular member is an enlarged handle portion that contains a battery and a switch. At the other end of the tubular member is an emitting area that will allow emissions to pass from inside the tubular member to the outside. A laser light source is provided within the tubular member. The laser light source could be in the red or infrared light spectrum. In one embodiment, the laser light source is located within the tubular member near the emitting end of the device. The laser may be positioned such that the light from the laser light source shines directly out the emitting area of the tubular member. The laser can be aligned such that the light shines out the end of the tubular member along its long axis, perpendicular to the long axis of any other angle. In an alternate embodiment, a mirror is provided to direct the light from the laser light source out the emitting area of the tubular mirror at a different angle than the angle of the light beam from the laser light source. In another embodiment of the emitter device the laser light source is located within the tubular member at a location near the enlarged portion and a distance away from the emitting area. A light conduit is provided to conduct the light from the laser light source to the emitting area of the tubular member. The light conduit can be a fiberoptic device. The light conduit may be a hollow tube. The light conduit may be used in conjunction with a mirror to adjust the angle of the light. The light conduit may be curved or bent near the emitting area for adjustment of the angle of the light.

Thus, the object of the invention is to provide a surgical site locating device and method which are accurate and precise, easy to use and low in cost.

DESCRIPTION OF THE DRAWINGS

The above and other objects, advantages and features of the invention will become more clear when considered with the following specification and accompanying drawings, wherein.

DETAILED DESCRIPTION OF THE INVENTION

Figure 1:
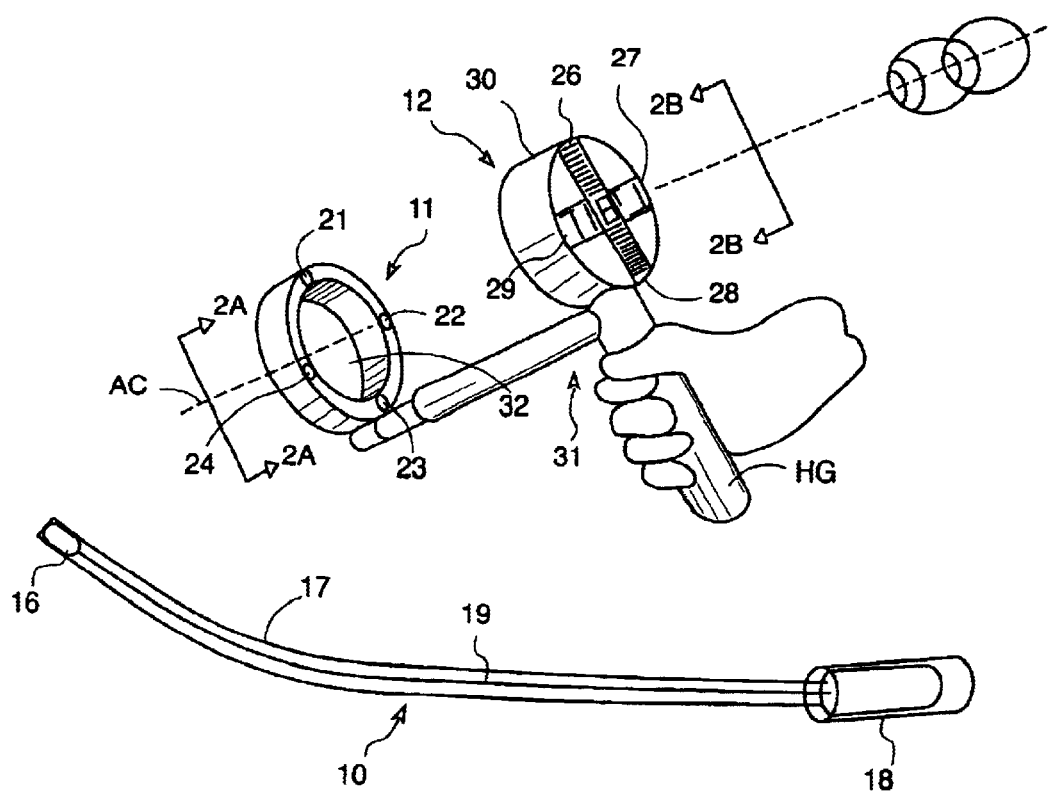
FIG. 1 is an isometric perspective view of the emitter or sender unit and an integrated sensor array and simplified display patterned on FIG. 1 of my U.S. Pat. No. 6,081,741.

Referring to FIG. 1, the invention includes the following elements: emitter element 10, sensor array 11 and display element 12. These elements are described in greater detail. Emitter assembly 10

Emitter assembly 10 includes a light-emitting diode (LED) 16 contained within a bio-compatible plastic tube 17 and connected to a battery 18 at the other end of the tube by electrical wires 19. Preferably, the plastic tube 17 is sealed at both ends. The electrical current may be interrupted from the LED by displacing the battery from the battery holder through the wall of the tube or by a switch (not shown). Laser light, directing mirrors and light conduits can be incorporated in the invention as shown in FIGS. 2–5 and described in the section entitled "Additional Light Emitter Sources."

Sensor array 11

The sensor array assembly 11 comprises an array of infrared light sensors 21, 22, 23, 24 (numbering at least three and preferably four) and a means of displaying the intensity of light which strikes the light sensors. The axial center AC of the sensors 21, 22, 23, 24 may be axially aligned with the axial center of display 12. A means of preconditioning the electrical signal from the light sensors may also be provided. Display element 12

The display element 12 is so arranged that the direction of the higher intensity light is clearly indicated. In one preferred embodiment, this is accomplished by having multiple signal indicators 26, 27, 28, 29, one for each sensor 21, 22, 23, 24 in the sensor array, the signal indicators 26, 27, 28, 29 being carried in a frame 30 and arranged in the display in such a way that mimics the relative location of the sensors in the sensor array thereby indicating the direction of relative movement between the sensor array 11 and emitter 10 to achieve accurate orientation and alignment of the center of the sensor array.

In one form of the invention, the array of light sensors 11 is contained within a handled assembly 31 which has a port 32 for surgical tool access in the axial center AC of the array 11 and a handle grip HG as shown in FIG. 1. In this form of the invention, the access port 32 can be used with a cutting tool, such as a surgical drill, to advance a surgical approach towards the emitter.

ADDITIONAL LIGHT EMITTER SOURCES

Figure 2A:
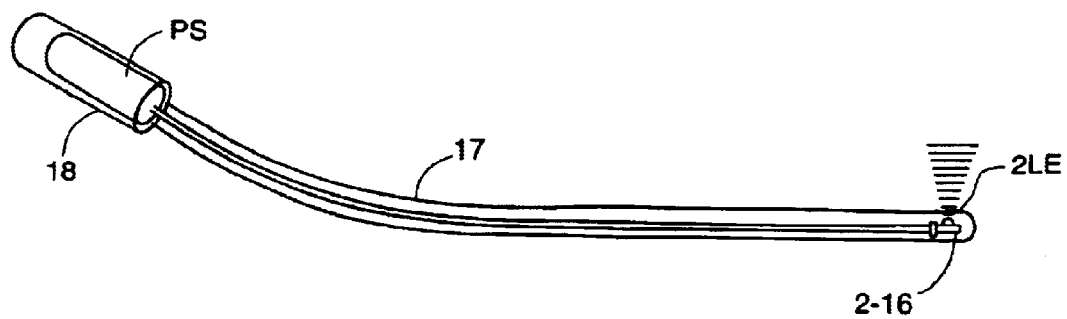
FIG. 2A is a modification illustrating a light emitting diode emitting light through a light-emitting area transverse to the axis of the catheter.
Figure 2B:
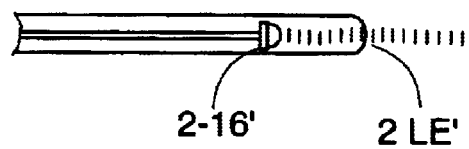
FIG. 2B is a partial view showing the LED mounting in the end of and directing light through a light-emitting area.

As shown in FIG. 2A, the light-emitting diode 2–16 can be oriented to direct light transversely through the catheter or tube 17. An area 2LE on the catheter 17 designated "emitting area" is for best emitting light in a given direction transverse of the axis of the catheter or tube 17. As shown in FIG. 2B, the light-emitting area 2LE' is at the end of the catheter and light is emitted along the tube axis.

Figure 3A:
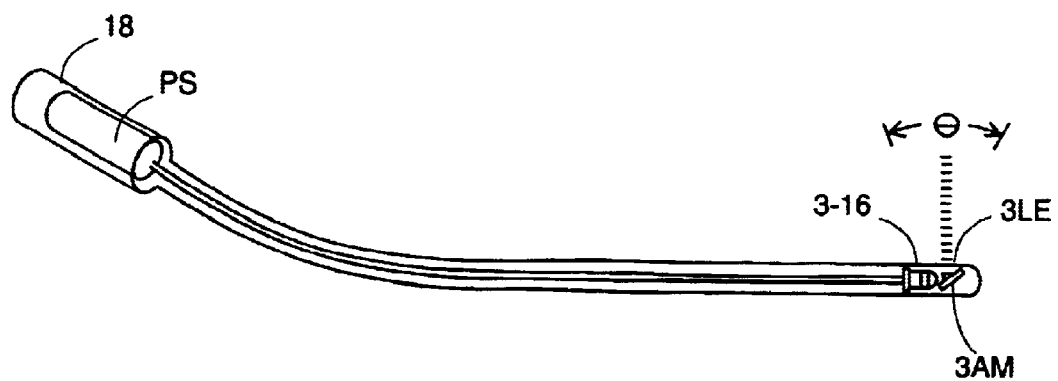
FIG. 3A is an embodiment of the invention in which a laser emitter is mounted in the end of the catheter, and a laser mirror redirects light in a given direction.

Referring now to FIG. 3A, the handle 18 is provided with a power supply PS for driving a laser emitter 3–16 which projects light against a reflecting mirror 3AM which directs light through an emitting area 3LE on the catheter or tube 17. Mirror 3AM can be pivoted so that the laser light beam can scan an arc Θ by rotation of the mirror 3AM.

Figure 3B:
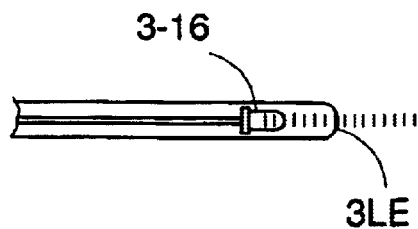
FIG. 3B is an illustration of the laser mounted in the end of the emitting laser light along the longitudinal axis thereof.
Figure 4A:
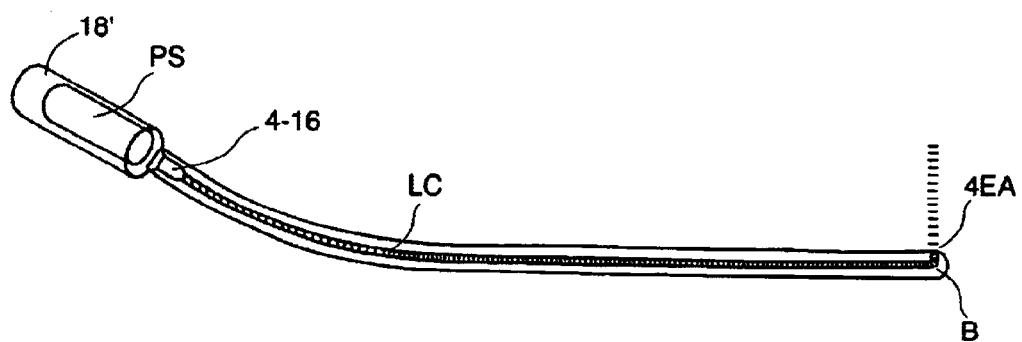
FIG. 4A is another embodiment of the invention in which a laser is mounted in the handle or adjacent the handle, and the catheter contains a fiberoptic light conduit with a bend at the end thereof at the light-emitting area.
Figure 4B:
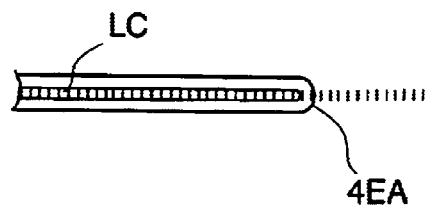
FIG. 4B illustrates that the light conduit has a light-emitting end and emits light directly along the axis thereof.
Figure 5:
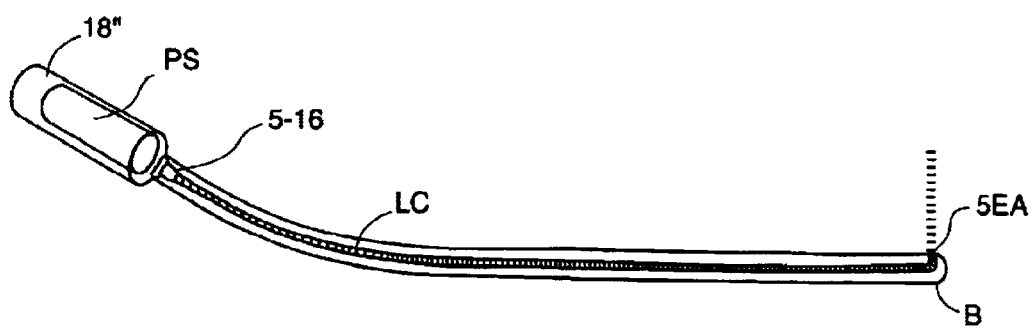
FIG. 5 is another embodiment in which a light-emitting diode is combined with a light conduit and has a bent end directing light through an emitting area in a given direction.

In FIG. 3B, a laser 3–16 is oriented to emit laser light through the light-emitting area at the end of the catheter. Note that in connection with FIG. 2B, the infrared light emitted by the light-emitting diode LED is focused in a beam. Note further that the beam from the two laser embodiments emit laser light in a very narrow beam. In the embodiment shown in FIGS. 4A, 4B and 5, a light conduit or fiberoptic conduit LC is used to couple light (whether from a laser or LED) from the handle 18' or handle area through the fiberoptic light conduit LC to an emitting area. In the case of FIG. 4A and FIG. 5, the fiberoptic conduit is bent at the end B so that the emitting end is aligned with the emitting area 4EA of the catheter. In FIG. 4B, the end of the catheter is transverse to the light-emitting area of the catheter.

In FIG. 5, a light-emitting diode LED is mounted in the handle 18", and infrared light from the light-emitting diode is conveyed through the light conduit to a bend area in the light conduit, and the light-emitting end is flush with the light-emitting area.

The mirror angle may be adjustable by a control link (not shown) to adjust the angle of light emission, and a light conduit may be curved near the light-emitting area for adjustment of the light-emitting angle.

Figure 6:
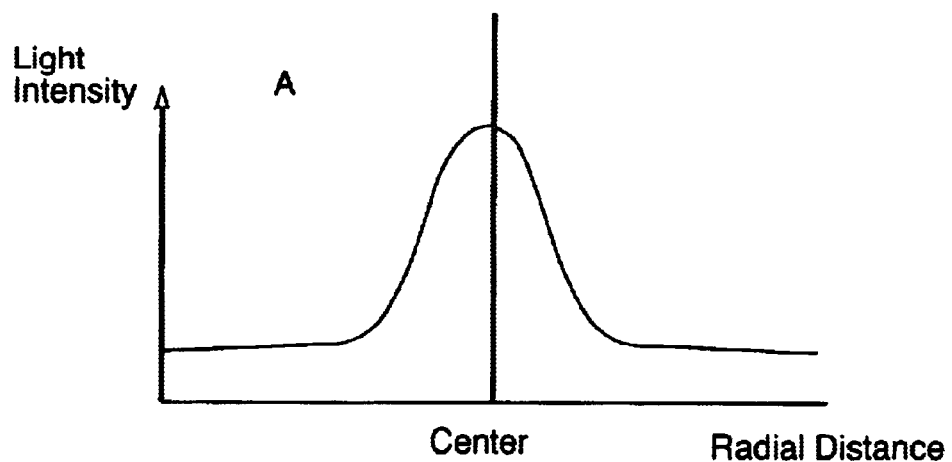
FIG. 6 is a graph showing the surface light intensity versus distance for a laser emitter.
Figure 7:
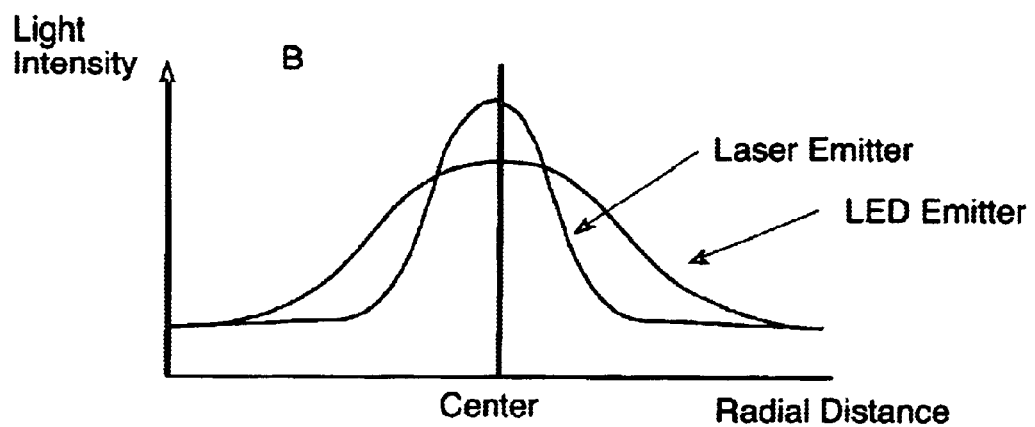
FIG. 7 is a graph showing the light intensity comparison of a laser emitter as opposed to an LED emitter.

The fundamental difference between the laser light and the light-emitting diode is illustrated in the graph shown in FIGS. 6 and 7. In FIG. 6, the graph illustrates the peak light at the center versus the radial distance from the center. FIG. 7 is a comparison of the laser emitter and the LED emitter relative to the center showing the sharp peak light emission of the laser emitter as compared to the LED emitter.

PRINCIPLE OF OPERATION

It has been well established that light, especially in the red and infrared spectrum can pass through biological tissue. As with any radiant energy, the intensity of the energy at any point is lessened as the distance from a point source is increased. This is caused both by the spreading out of the energy over a wider area as you move away from the source but also, as in the case of light through tissue, adsorption of the energy by the medium. The present invention uses these phenomena in a novel way to solve a persistent problem in surgery which is to precisely locate anatomical structures and locations through overlying tissue. This is done by providing an array of sensors 11, preferably four, in order to detect the gradient of light intensity, and the symmetry of that energy within the sensor array 11. The novel method for the layout and design of the sensors and display provide for a reproducible, precise, quick, intuitive, and easily learned way to locate the center of a field of light emanating from a point source and at low cost.

The invention therefore provides a simple and accurate means for indicating the direction of the emitter relative to the sensor array and indicating clearly when the sensor array is centered over the emitter. This enables surgeons to locate anatomical structures containing the emitter much faster and simpler than has previously been possible.

While the invention has been described in relation to preferred embodiments of the invention, it will be appreciated that other embodiments, adaptations and modifications of the invention will be apparent to those skilled in the art.

What is claimed is:

1. A guidance system for locating points in a living body having body passages therein comprising:
   a. a source of laser light for emitting light of a predetermined frequency and means for directing said laser light in a selected body passage and in a selected direction in said living body,
   b. a detector having a plurality of individual sensors mounted in a sensor array such that laser light from said source passing through tissue in said living body impinges on one or more of said sensor array and produces an electrical signal proportional to the laser light impinging thereon,
   c. a processor for processing intensity of laser light from said laser light source passing through said body tissue and falling on each sensor, respectively, in said sensor array, and
   d. an indicator display connected to said processor for indicating the relative intensity of laser light impinging on said sensors, respectively, as a function of the location of said laser light source in said living body.

2. The guidance system defined in claim 1 including a mirror for directing laser light in said selected direction.

3. The guidance system defined in claim 1 including a hollow laser light opaque rod having one or more apertures therein for passing laser light in said selected direction to said sensors.

4. A guidance system for locating a point in a living body having a passage therein as defined in claim 1, said source of laser light of a predetermined frequency and a light conduit having a light-receiving end and a light-emitting end means for introducing said light-emitting end into a selected passage in said living body.

5. The guidance system defined in claim 4 wherein said light-emitting end is bent and light is emitted from said bent end.

6. The guidance system defined in claim 4 including a mirror.

7. A surgical guidance method for locating a point in a living body having passages therein comprising the steps of:
   a. introducing a laser light source into a selected passage in said living body,
   b. providing a detector having a plurality of individual laser light intensity sensors mounted in a predetermined pattern and detecting laser light from said emitter passing through tissue in said living body which impinges on one or more sensors in said sensors in said predetermined pattern, and
   c. displaying the relative light intensity of laser light detected by each sensor in said predetermined pattern in such a manner to provide an accurate indication of the relative direction of movement to achieve alignment and orientation.

* * * * *